United States Patent

Schmidhammer et al.

Patent Number: 4,528,174
Date of Patent: Jul. 9, 1985

[54] METHOD FOR PREPARING HYDROGEN CHLORIDE FOR THE ETHYLENEOXICHLORINATION PROCESS

[75] Inventors: Ludwig Schmidhammer, Haiming/Marktl; Gerhard Dummer, Burgkirchen; Rudolf Strasser; Klaus Haselwarter, both of Burghausen; Hermann Klaus, Marktl; Eduard Pichl, Mehring, all of Fed. Rep. of Germany

[73] Assignee: Wacker-Chemie GmbH, Munich, Fed. Rep. of Germany

[21] Appl. No.: 614,530

[22] Filed: May 29, 1984

[30] Foreign Application Priority Data

Sep. 5, 1983 [DE] Fed. Rep. of Germany ....... 3331962

[51] Int. Cl.$^3$ .............................................. C01B 7/08
[52] U.S. Cl. .................................. 423/488; 423/481; 570/254; 570/255
[58] Field of Search ............... 423/481, 488; 570/241, 570/254, 255

[56] References Cited

U.S. PATENT DOCUMENTS

| | | | |
|---|---|---|---|
| 2,137,095 | 11/1938 | Peck | 423/488 |
| 2,196,246 | 4/1940 | Brown et al. | 423/488 |
| 2,377,669 | 6/1945 | Brown et al. | 570/241 |
| 3,496,243 | 2/1970 | Berkowitz et al. | 570/254 |
| 3,923,963 | 12/1975 | Rideout et al. | 423/481 |
| 3,989,806 | 11/1976 | Hyatt | 423/481 |
| 3,989,807 | 11/1976 | Hyatt | 423/481 |
| 4,018,880 | 4/1977 | Correia et al. | 423/481 |
| 4,031,149 | 6/1977 | Eden | 423/481 |
| 4,046,822 | 9/1977 | Severino | 570/251 |
| 4,113,786 | 9/1978 | Tsao | 423/488 |
| 4,169,862 | 10/1979 | Eden | 423/481 |
| 4,329,323 | 5/1982 | Shiozaki et al. | 423/488 |

FOREIGN PATENT DOCUMENTS

| | | | |
|---|---|---|---|
| 86387 | 12/1971 | Denmark | 570/255 |
| 2556521 | 3/1977 | German Democratic Rep. | |
| 42-3485 | 2/1967 | Japan | 570/255 |
| 46-3363 | 1/1971 | Japan | 570/254 |
| 196258 | 2/1924 | United Kingdom | 423/481 |
| 983032 | 12/1982 | U.S.S.R. | 423/488 |

*Primary Examiner*—John Doll
*Assistant Examiner*—Wayne A. Langel
*Attorney, Agent, or Firm*—Collard, Roe & Galgano

[57] ABSTRACT

A method for preparing hydrogen chloride resulting from chlorination reactions for use in the ethyleneoxichlorination process by reacting the chlorine contained in the hydrogen chloride with ethylene in the gaseous phase in the presence of carrier catalysts based on an iron-free transition metal chloride having an activity profile which increases in the flow direction, while maintaining the space-flow rates relatively high and the residence time of the gas in the reactor short. After discharge of the reaction product from the reactor the product is subjected to partial condensation advantageously performed in several steps.

4 Claims, No Drawings

METHOD FOR PREPARING HYDROGEN CHLORIDE FOR THE ETHYLENEOXICHLORINATION PROCESS

The invention relates to a method for preparing hydrogen chloride resulting from chlorination reactions for use in the ethyleneoxichlorination process, by reacting chlorine, which is contained in the hydrogen chloride, with ethylene in the vapor phase in the presence of carrier catalysts based on chlorides of transition metals, with the exclusion of iron chloride.

Hydrogen chloride is used in the production of dichloroethane in the oxichlorination process. This hydrogen chloride is obtained, in large amounts and also in the required purity, in the thermal cracking of dichloroethane to form vinyl chloride. In view of modern, integrated production systems, it is now desirable to use hydrogen chloride for oxichlorination reactions, which, e.g., is obtained from perchlorination reactions. However, hydrogen chloride from such sources contains in addition to perchlorinated compounds, e.g., carbon tetrachloride and perchloroethylene being present according to their partial vapor pressures, larger amounts of elementary chlorine—up to 20 molar-%. These impurities render the hydrogen chloride unsuitable for use in an oxichlorination process; it causes, for instance, chlorine/iron burn-up in the feed pipes. Moreover, the chlorine content creates operational problems at the compressor unit upstream the oxichlorination reactor. It is true that the difficulties can be overcome, but that involves high expenditures which renders the process uneconomical. In addition, chlorine promotes the grain disintegration of oxichlorination catalysts with the result that, within a short time, conditions have to be faced in the operation which lead to increased by-product formation in the oxychlorination process. A higher proportion of perchlorinated compounds, e.g., carbon tetrachloride, leads to similar catalyst damages.

In addition to a number of other physico-chemical and chemical methods, it has therefore been proposed to convert the chlorine entrained in the hydrogen chloride with ethylene into dichloroethane.

According to DE-AS No. 25 56 521, hydrogen chloride contaminated with chlorine is passed over an active carbon filter at an elevated temperature with an excess of ethylene, the chlorine reacting with the ethylene to form dichloroethane and the other impurities carried along according to their partial vapor pressures being eliminated by adsorption. Such active carbon filters are, however, very susceptible to plugging so that a plurality of such filters must always be available for parallel operation. In addition, regeneration of the filters requires expensive measures, as a result of which the proposed process is only economically useful when small amounts of impurities have to be eliminated from the hydrogen chloride.

According to DE-OS No. 22 51 696, chlorine is removed from a gaseous mixture by reaction of chlorine with ethylene in the presence of a Lewis acid, especially iron-III-chloride. Unfortunately, under the conditions set undesirable by-products are formed, such as ethyl chloride and trichloroethane, so that the reaction mixture has to be purified by distillation before being further processed.

According to DD-PS No. 86 387, the problem of obtaining sufficient selectivity of the reaction of chlorine with ethylene to form 1,2-dichloroethane is solved by using a carrier catalyst based on copper-II-chloride which contains other metal chlorides as promoters, diluting the reaction mixture with an inert gas and, furthermore, adding to the catalyst composition up to 80% by volume of an inert material having a high thermal conductivity, e.g., silicon carbide. In this manner, however, valuable, expensive reaction space is wasted and that results in low space-time performance. Due to the intensive dilution of the catalyst, it further becomes necessary to operate with comparatively high residence times in order to achieve complete conversion. As a consequence, large catalyst volumes are required to arrive at technically interesting throughputs. Since in practice temperatures of about 200° C. have to be maintained in order to use the catalyst space fully, one must accept uneconomically short life times for the catalyst.

It is therefore an object of the present invention to provide a method for the purification of hydrogen chloride which is contaminated by chlorine and chlorinated compounds.

It is a more particular object of the present invention to provide such a method wherein the chlorine contaminating the hydrogen chloride is reacted with ethylene to obtain 1,2-dichloroethane in a quantitative amount which can be removed, and, at the same time, eliminate chlorinated compounds being present according to their partial vapor pressures to an extent that the so-purified hydrogen chloride can be used in an ethyleneoxichlorination process.

It has now been found according to the invention that the chlorine contained in hydrogen chloride will be converted practically completely with ethylene to dichloroethane, with high selectivity to the 1,2-dichloroposition, when a carrier catalyst is used based on a transition metal chloride, and when the following conditions are observed: the carrier-catalyst has an increasing activity profile in the flow direction, the space-flow rates are relatively high, and short contact times are maintained.

The invention therefore concerns a method for preparing hydrogen chloride, obtained in chlorination reactions and still containing chlorine, for use in the ethyleneoxichlorination process, by reacting the chlorine with ethylene in the vapor phase in the presence of carrier catalysts based on a transition metal chloride, with the exclusion of iron chloride. According to the present method, chlorine contained in the hydrogen chloride is reacted at temperatures from 70°-150° C. and a pressure of 1.5-5 bar abs. with a molar excess of 5 to 20% of ethylene, in the presence of a carrier catalyst based on a transition metal chloride and having an activity profile rising in the flow direction, wherein space-flow rates (defined below) of 1000 h$^{-1}$ to 3000 h$^{-1}$ and contact times of 2–5 seconds are maintained. The reaction product after discharge from the reactor is subjected to a partial condensation while maintaining the temperature in at least one condensation step between −20 and −30° C.

Preferably, the reaction temperature is between 90° and 130° C. and the space-flow rates are from 1200 h$^{-1}$ to 1800 h$^{-1}$. The space-flow rate is defined as the amount expressed in volume of the gaseous reaction mixture at 0° C. and 760 Torr pressure (atmospheric pressure), which flows per hour and per liter of catalyst volume through the reaction system. Advantageously, the excess of ethylene, when calculated on the stoichiometrically present chlorine in hydrogen chloride, is 8–12 Mole-%.

As a matter of fact, the hydrogen chloride to be processed is obtained as an undesirable by-product in chlorination reactions and, in addition to chlorination products being present according to their partial vapor pressures, its chlorine component is present in an amount of up to 20 Mole-%. Examples of such chlorination processes are especially perchlorination processes of $C_1$ to $C_3$ hydrocarbons, and also chlorinations of aromatics and of acetic acid in the presence of acetic anhydride or acetyl chloride.

As mentioned above, according to the invention, the chlorine is converted by reaction with excessive ethylene to 1,2-dichloroethane. The ethylene is advantageously added shortly before the admission of the gas mixture to the reactor. The gas mixture may, if desired, be preheated to about the reaction temperature.

As also mentioned above, a carrier catalyst is applied which contains as an active component a transition metal chloride and, preferably, additional promoters. Examples of the active chlorides are especially copper-II-chloride, but also manganese-II-chloride, chromium-III-chloride, cobalt-II-chloride and lanthanum-III-chloride. Iron-III-chloride is specifically excluded, because it promotes an excessive amount of by-products. Suitable promoters are, e.g., the chlorides of potassium, magnesium, calcium and silver.

Carrier materials are inert materials, known per se, such as aluminum oxide, kieselgel, alumosilicates, and the like. The carrier materials are used in the shapes of balls, cones, cubes, hollow tubes and the like.

According to the invention, the catalyst exhibits an increasing activity profile in the direction of flow, i.e., the amount of active substance becomes larger with reference to the total weight of the catalyst, in the flow direction. With a given concentration of active substance at the reactor inlet of 5-7% by weight, concentration of the active substance increases up to the outlet of the reactor, continuously or discontinuously (e.g., in 2 to 4 reactor zones) up to 2.5-4 fold. The concentration of the promoters is generally a uniform 1.5 to 3.5% by weight compared to the total catalyst weight.

The reaction temperatures are maintained at 70°-150° C., and, preferably, at 90°-130° C. The pressure is 1.5 to 5 bar. The maintenance of the other parameters, space-flow rate and contact times of 2-5 seconds are effected in a manner known by those skilled in the art, e.g., by adjustment of the dimensions of the apparatus, particularly the choice of the lengths of the tubes and their cross-sections, and by the provision of an appropriate catalyst volume.

After the reaction product has been discharged from the reactor, it is subjected to a partial condensation at temperatures between $-20°$ and $-30°$ C. As a result, hydrogen chloride, ethylene and possibly other uncondensable components carried along according to their vapor pressures are separated from the chlorinated compounds, especially of 1,2-dichloroethane.

It is advantageous to carry out the partial condensation in at least two steps. For example, in the first condensation step, the reaction product is passed through a heat exchanger operated with water and maintained at a temperature of from about 20° to 40° C. The mixture which flows from the heat exchanger consists of condensed and uncondensed components which may then be collected in a gas/liquid separator. The uncondensed portion is passed through a second heat exchanger, operated, e.g., by Freon, in which, at a temperature from $-20°$ to $-30°$ C., a practically complete condensation of the condensable components of the reaction mixture takes place. The uncondensed exhaust vapor consisting substantially of hydrogen chloride is subsequently conveyed to an ethyleneoxichlorination apparatus, without any further purification being necessary.

The condensate obtained in the process according to the invention, essentially consisting of 1,2-dichloroethane, can likewise without further purification, be converted, e.g., via thermal cracking to vinyl chloride.

In the following, the invention will be more fully described, in a number of examples, but it should be understood that these are given by way of illustration and not by way of limitation.

EXAMPLE 1

3,884 $Nm^3/h$ of hydrogen chloride from a perchlorination process contaminated with 19 Mole-% of chlorine, 0.43 vol.-% of carbon tetrachloride and 45 ppm by vol. of perchloroethylene were preheated to 100° C. over a vapor jacket heater and, under a pressure control at 2.5 bars abs., were mixed immediately before entering a reactor with 810 $Nm^3/h$ of ethylene which was maintained under a pressure of 3 bars abs. and at a temperature of 40° C. The reactor consisted of a bundle of nickel tubes (1,570 tubes with an inside diameter of 27.5 mm and a length of 3,660 mm corresponding to a catalyst volume of 3,200 liters). The catalyst was placed in the nickel tubes. As carrier material, aluminum oxide was used, which was in the shape of balls having a size of 3–5 mm. The active material applied was copper-II-chloride. The activity profile increasing in the flow direction was realized by filling the first third of the reactor with copper-II-chloride of 6.5% by weight, the second third at the center of the reactor with 11% by weight, and the last third of the reactor with 19% by weight. Moreover, the carrier catalyst was uniformly impregnated with 2% by weight of potassium chloride. In the bottom and the top tube sheet of the reactor, insert saddle-shaped ceramic bodies were placed.

The nickel tubes were encased in an outer jacket which was filled with water as cooling medium for the dissipation of the heat developed during the reaction; the water had a temperature of 125° C. and a corresponding vapor pressure of 2.25 bars abs.

The space-flow rate was under normal conditions 1,698 $h^{-1}$, and the residence time of the reaction mixture in the reactor was 2.6 seconds. After leaving the reactor, the reaction mixture was fed through a heat exchanger filled with cooled water, where a partial condensation took place at 38° C. The mixture flowing out of the heat exchanger, consisting of condensed and uncondensed components, was collected in a gas-liquid separator. The uncondensed portion passed to a second heat exchanger operated by Freon, where at $-25°$ C. a practically complete condensation of the condensable components of the reaction mixture took place. The cold condensate was collected in a second gas-liquid separator whereas the uncondensed exhaust, substantially consisting of hydrogen chloride, was fed to a compressor station under a controlled pressure of 1.2 bars abs. and was thereafter introduced into an ethyleneoxichlorination process.

The exhaust stream (about 3,200 $Nm^3/h$) had the following composition:
  96.20 Mole-% hydrogen chloride
  1.50 Mole-% 1,2-dichloroethane
  2.23 Mole-% ethylene
  68 ppm by vol. carbon tetrachloride 8 ppm by vol. perchloroethylene
6 ppm by vol. ethyl chloride
2 ppm by vol. 1,1-dichloroethane The combined condensates from the two heat exchangers (about 3,050 kg/h) after having been released to atmospheric pressure, at a mixing temperature of 10° C., had the following composition:

96.18% by weight 1,2-dichloroethane
3.00% by weight carbon tetrachloride
290 ppm by weight perchloroethylene
316 ppm by weight ethylene
7,380 ppm by weight hydrogen chloride
44 ppm by weight ethyl chloride
20 ppm by weight 1,1-dichloroethane This condensate could be combined without further purification with 1,2-dichloroethane, which was obtained from an ethyleneoxichlorination unit, and directly fed into a furnace for obtaining vinyl chloride by thermal cracking.

The space-time performance of the reactor was 1,019 kg of 1,2-dichloroethane per m³ catalyst and hour. The chlorine conversion was almost 100%, the selectivity relating to the formation of 1,2-dichloroethane was 99.9%. Even after two years there were no signs of an inactivation or disintegration of the catalyst.

EXAMPLE 2

A nickel tube having a length of 350 cm and an inside diameter of 25 mm, corresponding to a catalyst volume of 1,715 m³ was used as the reactor. The nickel tube was encased by a jacket through which oil was pumped whose temperature was maintained at 85° C. by a thermostat. The tube was filled with a carrier catalyst, the carrier material consisting of kieselgel balls 5 mm in size. The activity profile of the catalyst, increasing in the direction of flow, was characterized by the following filling schedule:

First third (reactor inlet) 3% by weight $CuCl_2$ + 3% by weight $MnCl_2$ + 3% by weight KCl
Second third (reactor center) 6% by weight $CuCl_2$ + 6% by weight $MnCl_2$ + 3% by weight KCl
Last third (reactor exit) 9% by weight $CuCl_2$ + 9% by weight $MnCl_2$ + 3% by weight KCl Into the reactor, hydrogen chloride with a chlorine content of 12 Mole-% at a pressure of 1.5 bars abs. was introduced in an amount of 1,900 Nl/h together with 255 Nl/h of ethylene. The reaction mixture leaving the reactor was condensed at −25° C.

The condensate obtained amounted to 980 g/h and had the following composition:

96.45% by weight 1,2-dichloroethane
0.03% by weight ethylene
3.52% by weight hydrogen chloride The uncondensed gas exhaust (Amount: 1,699 Nl/h) contained:

97.49 Mole-% hydrogen chloride
0.83 Mole-% 1,2-dichloroethane
1.68 Mole-% ethylene The space-time performance was 588 g 1,2 dichloroethane per one liter catalyst volume and hour. The space-flow rate was 1,257 $h^{-1}$ under normal conditions and the residence time of the reaction mixture in the reactor was 3.7 seconds. The chlorine conversion and the selectivity concerning 1,2-dichloroethane formation was 100% throughout.

COMPARISON EXAMPLES 1-6

The method of Example 2 was repeated with the following changes: Hydrogen chloride was introduced into the reactor with a chlorine content of 15 Mole-%. Furthermore, the space-flow rates and the residence times in the reactor were changed as indicated in the table which follows.

TABLE 1

| TEST NO. | SPACE-FLOW RATE ($h^{-1}$) | RESIDENCE TIME (sec.) | TEMPERATURE (°C.) | CHLORINE CONVERSION (%) | SELECTIVITY (%) | SPACE-TIME PERFORMANCE (g/l · h) |
|---|---|---|---|---|---|---|
| 1 | 450 | 8 | 80 | 99.4 | 99.6 | 277 |
| 2 | 670 | 1.5 | 80 | 99.2 | 99.5 | 444 |
| 3 | 670 | 4.2 | 150 | 99.5 | 99.3 | 444 |
| 4 | 670 | 4 | 200 | 99.6 | 98.9 | 444 |
| 5 | 478 | 7 | 80 | 99.5 | 99.6 | 317 |
| 6 | 209 | 16 | 80 | 99.6 | 99.7 | 139 |

The results of tests 1, 5 and 6 show that despite increased residence times, at space-flow rates below 1,000 $h^{-1}$, the chlorine conversion cannot be rendered quantitative and that the space-time performances are considerably lower than with the process according to the invention. Tests 2, 3, and 4 show, moreover, that with rising temperature at space-flow rates below 1,000 $h^{-1}$ the selectivity of the reactions as regards the formation of 1,2-dichloroethane drops.

For all the comparison tests it can be stated that a chlorine conversion of only 99.6% indicates that in the hydrogen chloride after the reaction with ethylene there are still 600 ppm by vol. of chlorine present, which prevents the use of the so-obtained hydrogen chloride in an ethyleneoxichlorination process.

While only several embodiments and examples of the present invention have been described, it is obvious that many changes and modifications may be made thereunto, without departing from the spirit and scope of the invention.

What is claimed is:

1. A method for purifying hydrogen chloride obtained in chlorination reactions and still containing up to 20 mole % elementary chlorine, to permit its direct use in an ethyleneoxichlorination process, comprising the steps of:

reacting said hydrogen chloride containing said chlorine with ethylene in the vapor phase at a temperature from 70° C.–150° C., a pressure of 1.5–5 bars absolute and with a molar excess of 5 to 20% of ethylene, said reaction being conducted in a reactor in the presence of a carrier catalyst comprising an iron-free transition metal chloride which is arranged so as to provide an activity profile of the catalyst which increases in the flow direction, while maintaining in said reactor space-flow rates of from 1,000 $h^{-1}$ to 3,000 $h^{-1}$ and gas-catalyst contact times of from 2 to 5 seconds; and subjecting the reaction product after discharge from the reactor to partial condensation comprising at least one condensation step during which the temperature is maintained between −20° C. and −30° C.

2. The method of claim 1, wherein the reaction temperature is maintained between 90° and 130° C.

3. The method of claim 1, wherein the space-flow rate is maintained between 1,200 h$^{-1}$ and 1,800 h$^{-1}$.

4. The method of claim 1, additionally including the step of obtaining the hydrogen chloride to be processed from a perchlorination process.

* * * * *